United States Patent [19]

Tsujino

[11] Patent Number: 5,690,111
[45] Date of Patent: Nov. 25, 1997

[54] ULTRASOUND DIAGNOSTIC APPARATUS

[75] Inventor: Hiroyuki Tsujino, Otawara, Japan

[73] Assignee: Kabushiki Kaisha Toshiba, Kawasaki, Japan

[21] Appl. No.: 574,695

[22] Filed: Dec. 19, 1995

[30] Foreign Application Priority Data

Dec. 27, 1994 [JP] Japan ................................. 6-325568

[51] Int. Cl.$^6$ ........................................................ A61B 8/06
[52] U.S. Cl. ........................... 128/660.04; 128/660.05; 128/661.1
[58] Field of Search ..................... 128/660.07, 660.04, 128/661.01, 661.07–661.1

[56] References Cited

U.S. PATENT DOCUMENTS

| | | | |
|---|---|---|---|
| 3,954,098 | 5/1976 | Dick et al. ......................... | 128/660.04 |
| 4,790,322 | 12/1988 | Iinuma . | |
| 5,322,066 | 6/1994 | Miyataka et al. .............. | 128/660.01 X |
| 5,425,365 | 6/1995 | Iinuma ........................... | 128/661.09 X |
| 5,535,748 | 7/1996 | Byrne et al. ...................... | 128/660.07 |
| 5,551,434 | 9/1996 | Iinuma ............................ | 128/661.09 |

*Primary Examiner*—Francis Jaworski
*Attorney, Agent, or Firm*—Oblon, Spivak, McClelland, Maier & Neustadt, P.C.

[57] ABSTRACT

An ultrasound diagnostic apparatus comprises an ultrasonic transducer and a transmitter/receiver circuit for scanning a plane section of a human body under examination with ultrasonic beams repeatedly and with a given frame period to thereby obtain receiving signals, an ultrasonic image producing circuit responsive to the receiving signals for producing ultrasonic images successively and with the frame period, an image memory unit for storing ultrasonic images corresponding to multiple frames along with time information, a setting section for setting a period of interest, a CPU for reading a sequence of ultrasonic images corresponding to the set period of interest from the image memory unit selectively and with the frame period, an overlaid image producing circuit for producing an overlaid image containing an ROI marker and outputting it repeatedly and with the frame period, a frame combining circuit for combining each of the ultrasonic images and the overlaid image which are supplied synchronously with each other into one frame, a display monitor for displaying the ultrasonic images with which the overlaid image was combined as moving images, a CPU for changing the position of the ROI marker in the overlaid image, and a measuring circuit for obtaining measured values in the position of the ROI marker.

9 Claims, 4 Drawing Sheets

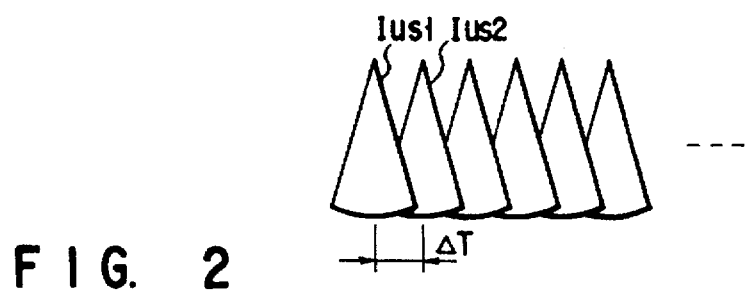
F I G. 2
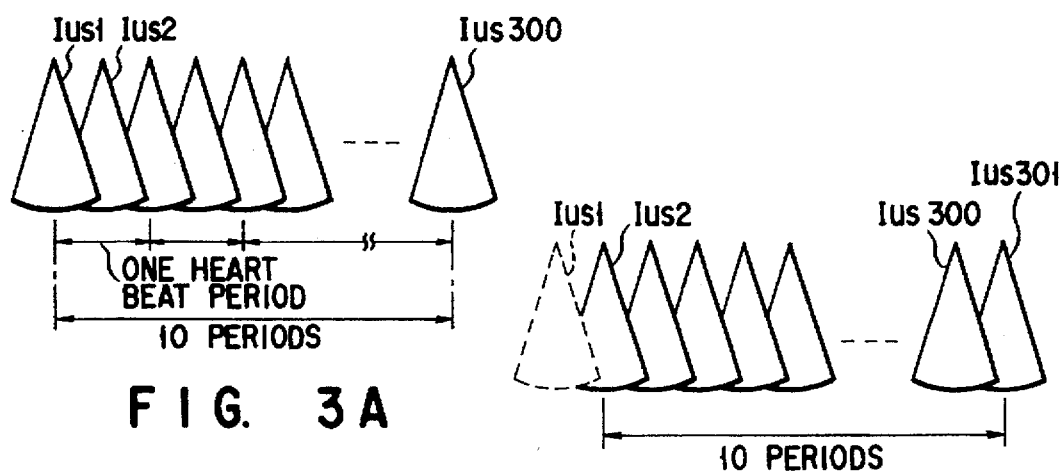
F I G. 3A
F I G. 3B
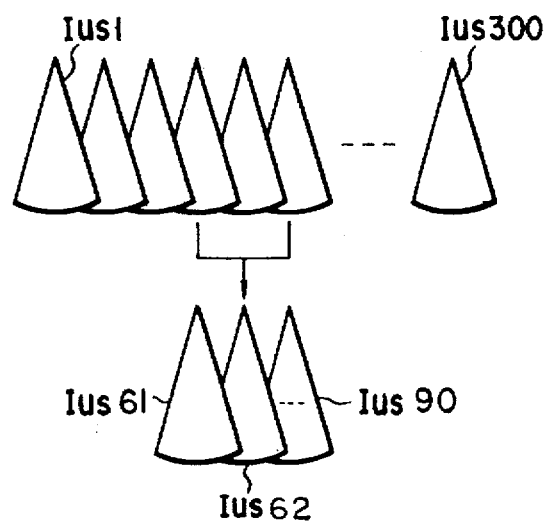
F I G. 4A
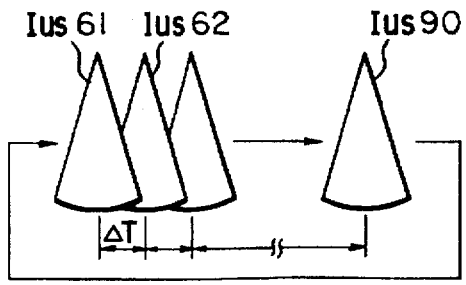
F I G. 4B

ULTRASOUND DIAGNOSTIC APPARATUS

BACKGROUND OF THE INVENTION

1. Field of the Invention

This invention relates to an ultrasound diagnostic apparatus which is capable of measuring a cardiac output and the like.

2. Description of the Related Art

In recent years, the importance of quantification has increased in the field of ultrasound diagnosis. Measurement items are blood flow rate (bloodstream volume), blood flow velocity, reflection strength, distance, area, capacity, and the like. For diagnosis of the function of the heart or the like, changes of measured values for these items with respect to time are effective. The reflection strength is related to the pixel values in a B-mode image. A time curve of pixel values is called a time density curve (TDC) and has become widespread. M-mode images, changes in pulsed Doppler frequency spectrum with time and the like are also employed for functional diagnosis.

The ultrasound diagnostic method is superior in real-time image display to other modalities such as CT (Computerized Tomography) and the like. However, the real-time image display makes the measuring operations troublesome. That is, an operator must set an ROI marker representing a region of interest (ROI) in a proper place on an image by operating a mouse or a trackball while holding an ultrasonic transducer with one hand. This makes it difficult for the operator to hold the ultrasonic transducer firmly in the optimum position. In addition, it becomes difficult for the operator to set the ROI in the optimum place. As a result, the precision of the measurement will be decreased.

Such a problem can be solved by the use of an image memory. Suppose the case where a measurement is made of an amount of blood (i.e., stroke volume or cardiac output) pumped into the artery during a period of time the heart contracts once. A plurality of frames of velocity image data is successively generated during one heart beat period synchronously with an electrical change in the heart, then stored in the image memory. Since there is no need of setting the ROI marker, the operator can devote himself or herself to holding the ultrasonic transducer during scanning. After the termination of scanning, the velocity image information is read out of the image memory, then displayed as moving images. A specific image is displayed in freeze-frame state and then the ROI marker is set in a proper place on the image of the freeze frame. Since there is no need of holding the probe, the operator can devote himself or herself to setting the ROI marker.

In the prior art, however, only images during a specific heart beat period stored in the image memory can be utilized for observation of moving images and measurement of a cardiac output. Even if images corresponding to a plurality of heart beat periods were stored in the image memory, the stroke volume for a certain beat could not be measured because there is no indication of which heart beat period each image corresponds to.

In addition, a problem is encountered in setting the ROI marker. In this case as well, suppose the measurement of a cardiac output. It is assumed here that velocity images corresponding to 30 frames are produced during one heart beat period. In order to measure a cardiac output, it is required to set the ROI marker to cross the valve of the heart. It is assumed that the section of the vane is circular. An instantaneous cardiac output is calculated by integrating a velocity profile associated with the ROI marker with respect to the sectional area of the vane. The instantaneous cardiac output is calculated for each of 30 frames of velocity images. The cardiac output is calculated by integrating instantaneous outputs of different time phases with respect to time.

The position and size of the vane vary with the motion of the heart. In order to increase the precision of measurement of the cardiac output, therefore, it is required to set an individual ROI marker for each of 30 frames of velocity images. However, this work is very time-consuming. In practice, the ROI marker set on a certain image in freeze-frame state is used in common for the other frames. The ROI, marker is not optimal for any other image, and thus, the precision of measurement of a cardiac output will be decreased.

SUMMARY OF THE INVENTION

It is an object of the invention to provide an ultrasound diagnostic apparatus which permits moving images during any heart beat period to be reproduced and an ROI marker to be set easily in a proper position in the moving images, and which can therefore measures various values useful for diagnosis.

According to the present invention there is provided an ultrasound diagnostic apparatus comprising: means for scanning a plane section of a human body under examination by ultrasound waves repeatedly and with a given period to thereby obtain receiving signals; ultrasonic image producing means responsive to said receiving signals for producing ultrasonic images successively and with said given period; storing means for storing ultrasonic images corresponding to multiple successive frames along with time information; setting means for setting a period of interest; readout means responsive to said time information for reading a sequence of ultrasonic images which is a part of said ultrasonic images successively produced and corresponds to said period of interest from said storing means selectively and with said given period; overlaid image producing means for producing an overlaid image containing an ROI marker and outputting said overlaid image repeatedly and with said given period; combining means for combining each of said ultrasonic images corresponding to said period of interest and said overlaid image which are supplied synchronously with each other into one frame; displaying means for displaying said ultrasonic images combined with said overlaid image as moving images; position changing means for changing the position of said ROI marker in said overlaid image so that said ROI marker will shift on said moving images; and measuring means for obtaining measured values in the position of said ROI marker.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate a presently preferred embodiment of the invention and, together with the general description given above and the detailed description of the preferred embodiment given below, serve to explain the principles of the invention.

FIG. 2 is a diagram for use in explanation of the production of ultrasonic images;

FIGS. 3A and 3B are diagrams for use in explanation of the operation of storing ultrasonic images into the image memory unit of FIG. 1;

FIGS. 4A and 4B are diagrams for use in explanation of the operation of reading (reproducing) ultrasonic images from the image memory unit;

DETAILED DESCRIPTION OF THE PREFERRED EMBODIMENTS

Figure 1:
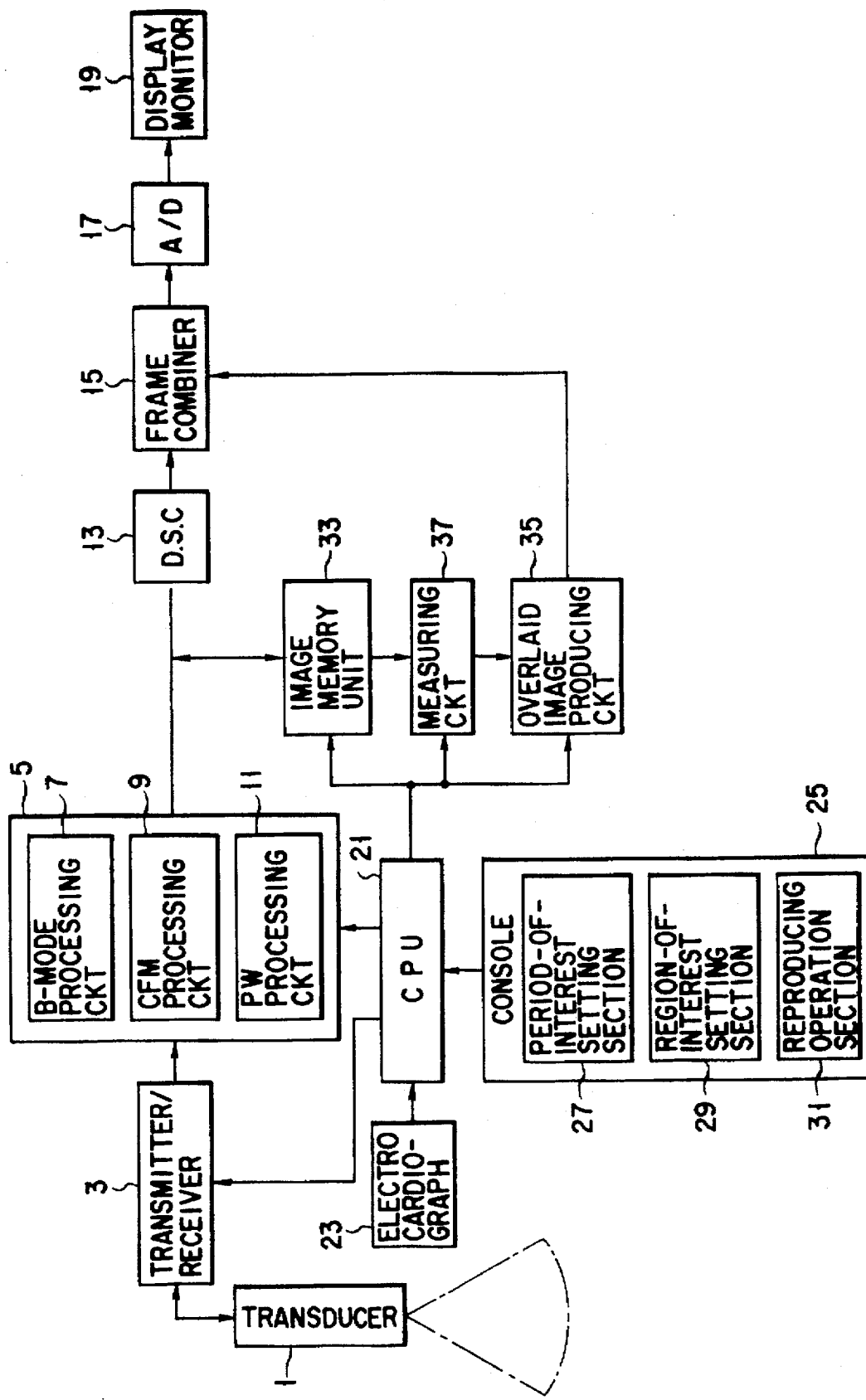
FIG. 1 is a block diagram of an ultrasound diagnostic apparatus embodying the present invention.

Referring now to FIG. 1, there is shown in block diagram form an arrangement of an ultrasound diagnostic apparatus embodying the invention. Using a CPU 21 as its control center the ultrasound diagnostic apparatus is arranged as follows. A transmitter/receiver circuit 3 has transmitting and receiving systems. The transmitting system has a clock generator, a rate pulse generator, a transmission delay circuit, and a pulser. The frequency of clock pulses generated by the clock generator is converted by the rate pulse generator to rate pulses of 5 KHz. The rate pulses are distributed to a plurality of channels, then applied to the transmission delay circuit. The transmission delay circuit provides a different delay time to rate pulses corresponding to each channel in order to focus ultrasound waves into a beam and swing the resulting ultrasound beam. The pulser includes a plurality of pulse drivers for each of channels. Each pulse driver provides a high-frequency voltage pulse at the time of receipt of a rate pulse. Upon receipt of voltage pulses, the transducer 1 transmits ultrasound waves to a human body under examination. The ultrasound waves are reflected by the boundary between acoustic impedances and received by the transducer 1. The receiving system is equipped with a preamplifier, a receive delay circuit, and an adder. The signals from the transducer 1 are sent via the preamplifier to the receive delay circuit, which provides different time delays to signals of the respective channels in order to obtain reflected components from a specific direction. The delayed signals are summed in the adder, whereby a received signal is obtained.

The transmitter/receiver circuit repeats the transmission/reception of ultrasound waves while changing the transmit time delays and receive time delays in a given cycle in order to scan a plane section of a human body under examination with a predetermined frame period (=1/fr where fr is the number of frames per second).

The received signals output from the transmitter/receiver circuit 3 are sent to an ultrasound image producing circuit 5, which comprises a B-mode processing circuit 7, a CFM processing circuit 9, and a PW processing circuit 11. The B-mode processing circuit 7 includes a detector and a logarithmic converter so as to produce B-mode image (tissue tomography image) data. The CFM processing circuit 9 includes a quadrature-phase detector, a lowpass filter, an MTI filter, an auto-correlation detector, and an operations unit so as to produce blood flow image data containing various pieces of blood flow information such as average velocity, dispersion, power and the like. The PW processing circuit 11 includes a sample and hold circuit, a bandpass filter, and a fast Fourier transform circuit in order to obtain a spectrum image representing changes in frequency spectrum at a point of interest with respect to time. B-mode images, blood flow images and spectrum images are generally called ultrasonic images.

Ultrasonic image data produced by the ultrasonic image producing circuit 5 is sent via a digital scan converter (DSC) 13, a frame combiner 15, and an analog to digital (A/D) converter 17 to a display monitor where it is displayed as moving images.

The CPU 21 stores the ultrasonic image data produced by the ultrasonic image producing circuit 5 in the image memory unit 33 together with information about the times when the received signals for that image data are acquired. The image memory unit 33 has a capacity for storing n frames of ultrasonic image information which correspond to several seconds.

An electrocardiograph 23 is connected to the CPU 21. Based on an electrocardiogram waveform from the electrocardiograph 23, the CPU 21 obtains heart time-phase information about the time that has elapsed from the R wave in the electrocardiogram and heart-beat number information representing how many times the heart has beaten from the start of a scan. The time information described previously contains these heart time-phase information and heart-beat number information.

To the CPU is connected an operating console 25, which is equipped with a period-of-interest setting section 27, a region-of-interest setting section 29, and a reproducing operation section 31. Various reproduction-related instructions for the start of reproduction, the stop of reproduction, the start of loop reproduction and the like are entered through the reproducing operation section 31.

When an operator operates the period-of-interest setting section 27, a period of interest is selected and the corresponding ultrasonic images are obtained. The images for this period are reproduced in the form of, for example, a systole of the heart. When a reproduction starting instruction or a loop reproduction starting instruction is entered by the operator from the reproducing operation section 31, the CPU 21 selects some ultrasonic images that are included within the period of interest thus set from among a plurality of frames of ultrasonic image information stored in the image memory unit 33 and sequentially reads them from the memory unit only once or repeatedly with the same frame period as when scans were made. Thereby, the ultrasonic images within the period of interest are reproduced in the form of moving images on the display unit 19.

An overlaid image generating circuit 35 repeatedly produces overlaid image data containing an ROI marker representing an region of interest with the same frame period as when scans are made and sends it in sequence to the frame combiner 15 in synchronization with ultrasonic image information. The overlaid image data is combined with the ultrasonic image information in the frame combiner 15. Thereby, the ROI marker is displayed superimposed on moving ultrasonic images on the display unit 19. When the operator operates the region-of-interest setting section 29 including a mouse or trackball to shift the ROI marker to a desired place on the ultrasonic image over a desired length, a region of interest (ROI) having the desired length is set up in the desired position. The CPU 21 reads pixel value data (velocity data) of pixels located on the ROI marker in each frame of ultrasonic image information reproduced as moving images from the image memory unit 33 into a measuring circuit 37. Also, the CPU 21 feeds position information of the ROI marker into the measuring circuit 37.

The measuring circuit 37 obtains various measured values from the pixel value data from the image memory unit or the position information. The measured value data is sent from the measuring circuit 37 to the overlaid image producing circuit 35. The overlaid image producing circuit 35 writes the measured values from the measuring circuit 37 into a preselected area of the overlaid image.

The operation of the apparatus of the invention will be described hereinafter. The transmitter/receiver circuit 3 drives the transducer 1 to scan a plane section of a human body under examination with a given frame period. As shown in FIG. 2, ultrasonic image information Ius1, Ius2, . . . is successively produced by the ultrasonic image producing circuit 5 with the same frame period $\Delta T$ as when scans are made.

The ultrasonic image information produced by the ultrasonic image producing circuit 5 is fed to the display monitor 19 through the DSC 13, the frame combiner 15 and the A/D converter 17, then displayed in real time as moving images.

The ultrasonic image information produced by the ultrasonic image producing circuit 5 is sent to the image memory unit 33 and stored therein together with time information about the times when received signals for that image data was acquired. If scans are made for a given period of time, the image memory unit 33 will become full of, for example, 300 frames of ultrasonic image information corresponding to 10 seconds or 10 periods as shown in FIG. 3A. If a further scan is made, the least recent ultrasonic image data Ius1 will be discarded or erased and, instead, the most recent ultrasonic image data Ius301 will be written into the image memory unit as shown in FIG. 3B. Thus, the CPU 21 constantly stores the most recent 300 frames of ultrasonic image information into the image memory 33.

At the termination of scans, 300 frames of ultrasonic image information which are the most recent at that time have been stored in the image memory unit 33. For convenience of illustration the 300 frames of image information will be denoted by Ius1, Ius2, . . . , and Ius300.

For example, the third heart beat period from the start point (Ins 61) and end point (Ins 90) of a period of interest by the operator operating the period-of-interest setting section 27. Next, a reproduction starting or loop reproduction starting instruction is entered by the operator operating the reproducing operation section 31. As shown in FIG. 4B, a sequence of ultrasonic image information Ius61 through Ius90 during that period of interest is read selectively and with the same frame period $\Delta$ as when scans were made from the image memory unit 33 into the DSC 13 on the basis of the time information under the readout control of the CPU 21. Thereby, the ultrasonic image information Ius61 through Ius90 during the period of interest is displayed as moving images on the display unit 19 only once or repeatedly as shown in FIG. 4B. The speed of reproducing the image information can be varied.

Heart time-phase information and heart-beat number information are attached to the ultrasonic image data for each frame. Thus, a period of interest can be specified by using the information and various convenient setting methods are possible. For example, a period of interest can be set as a heart contraction or expansion period. Namely, the contraction or expansion period of interest can be set by specifying how many contraction or expansion periods there are before that contraction or expansion period of interest. The heart contraction or expansion period can be specified on the basis of the heart time-phase information. Thus, it becomes possible to reproduce ultrasonic images during any period of interest by storing ultrasonic image data corresponding to a plurality of periods in the image memory unit 33 with time information attached thereto.

Figure 5A:
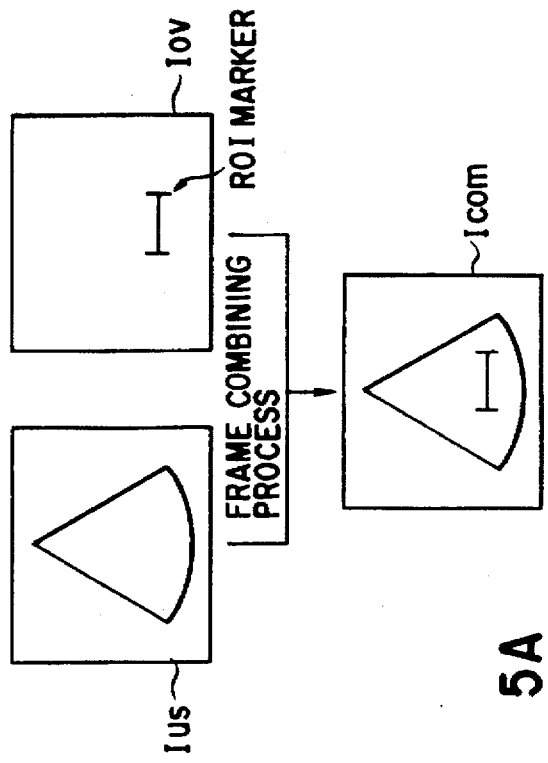
FIGS. 5A and 5B are diagrams for use in explanation of the operation of combining an ultrasound image and an overlaid image by the frame combiner of FIG. 1.
Figure 5B:
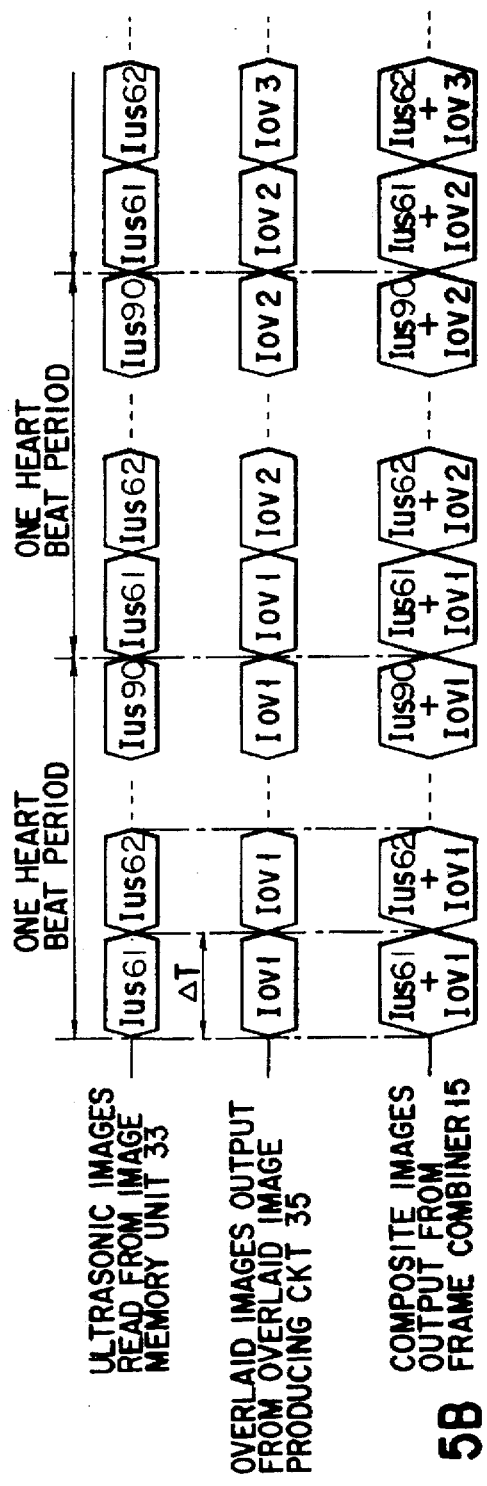

As shown in FIGS. 5A and 5B, overlaid image data Iov containing an ROI marker indicating a region of interest is repeatedly produced by the overlaid image producing circuit 15 with the same frame period as when scans are made and then combined with the ultrasonic image data Ius61 and so on in the frame combiner 15. Thereby, the ROI marker is displayed superimposed on moving images on the display monitor 19.

Figure 6A:
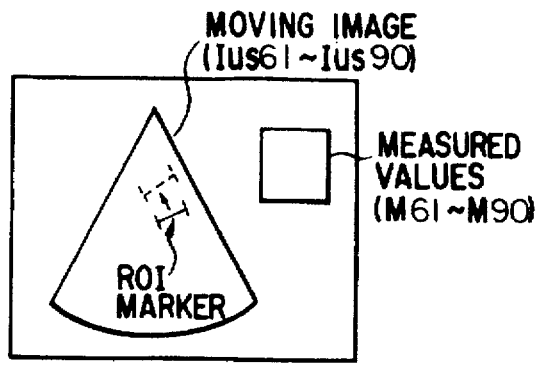
FIGS. 6A and 6B show on-screen images of the display monitor of FIG. 1.
Figure 6B:
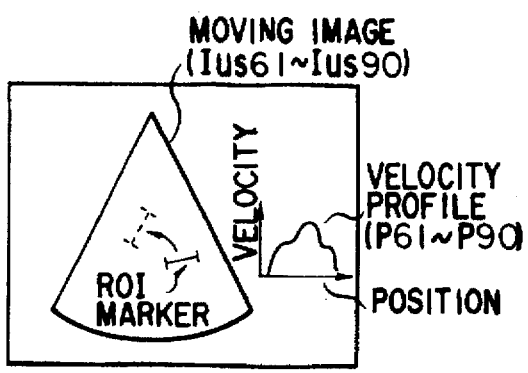

When the region-of-interest setting section 29 is operated by the operator, new position data for the ROI marker is supplied from the CPU 21 to the overlaid image producing circuit 35, which, in turn, produces new overlaid image data Iov2 on the basis of the new position data. The position of the ROI marker in the overlaid image data Iov2 is shifted from that in the overlaid image data Iov1. The overlaid image data Iov2 is combined with ultrasonic image data in the frame combiner 15. Thereby, as shown in FIGS. 6A and 6B, the ROI marker will shift on moving images which keep their motion.

The operation of the region-of-interest setting section 29 is terminated when the ROI marker is set to the optimum place and length such that it crosses the vane of the heart completely. Thereby, a region of interest is set.

By displaying ultrasonic image data during a period of interest in the form of motion images and superimposing an ROI marker on the images in the above manner, the following effects can be achieved. In the prior art, since setting an individual region of interest for each of frames during a period of interest is very troublesome and time-consuming, a specific frame of ultrasonic image information is displayed in the freeze state and then a region of interest is set on the freeze image. Based on the position and length of that region of interest, individual measurement is made for each of frames within a period of interest. Therefore, the possibility exists that a region of interest may be set to a very undesirable position and length in other frames than a freeze frame within a period of interest. For such frames the measurement precision will be considerably reduced. In the present invention, however, since the ROI marker is displayed on moving images, the positional relation between the ROI marker and an ultrasonic image of each frame can be determined easily. Therefore, a region of interest can be set, in a short period of time, to a desirable place and length for each of frames within a period of interest.

When a region of interest is set, pixel value data (velocity data) of a pixel group on the region of interest in each of frames within a period of interest is selectively read by the CPU 21 from the image memory unit 33 into the measurement circuit 37. The position information of the region of interest is also fed from the CPU 21 into the measurement circuit 37.

On the basis of pixel value data (velocity data) from the image memory unit 33, instantaneous bloodstream volumes M61 to M90 and velocity profiles P61 to P90 are measured by the measurement circuit 37 for respective individual frames (heart time phases). As shown in FIG. 6B, the velocity profile is a plot of the blood-flow velocity values of pixels located on a region of interest with the abscissa as position and the ordinate as velocity.

The measured-value data thus obtained by the measurement circuit 37 for each heart time phase is sent to the overlaid image producing circuit 35, which, in turn, produces a number of frames of overlaid images of varying heart time phases. Into a preselected area of an overlaid image for each heart time phase are written the measured values for the corresponding heart time phase.

In synchronization with ultrasonic image data read out of the image memory unit 33, overlaid image data corresponding in heart time phase to the ultrasonic image data is outputted from the measurement circuit 37 to the frame combiner 15 with a given frame period ΔT under the control of the CPU 21. Thereby, an ultrasonic image and measured values (e.g., velocity profile) corresponding in heart time phase to that image are displayed simultaneously on the same screen of the display monitor 19. That is, the measured profile and the like are displayed and changed with the motion of moving images. Thus, the operator can grasp the changes of measured profile or the like with respect to time while watching moving images.

Moreover, a cardiac output is calculated by the measurement circuit 37 from instantaneous bloodstream volumes during the same heart beat period by time integration. Furthermore, a time density curve is obtained by the measurement circuit 37 from changes with time of a measured value obtained with each heart time phase, for example, an instantaneous bloodstream volume.

In addition, at least one of distance, area and capacity is calculated by the measurement circuit 37 on the basis of the position information of a region of interest.

The distance, area, capacity, stroke volume and time density curve are written into all overlaid images in the overlaid image producing circuit 35 under the control of the CPU 21. When values are measured of all frames designated, the reproducting of moving images is stopped. The values measured are displayed. Among these values is the stroke volume calculated from the sum of the amounts of blood which flowed while the frame were taken.

Figure 7A:
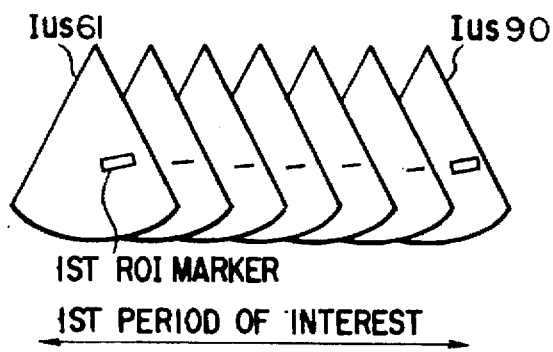
FIGS. 7A, 7B and 7C are diagrams for use in explanation of an application of the present embodiment.
Figure 7B:
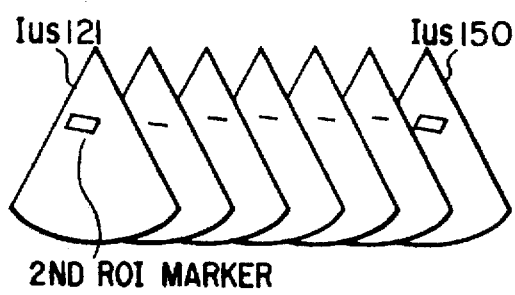
Figure 7C:
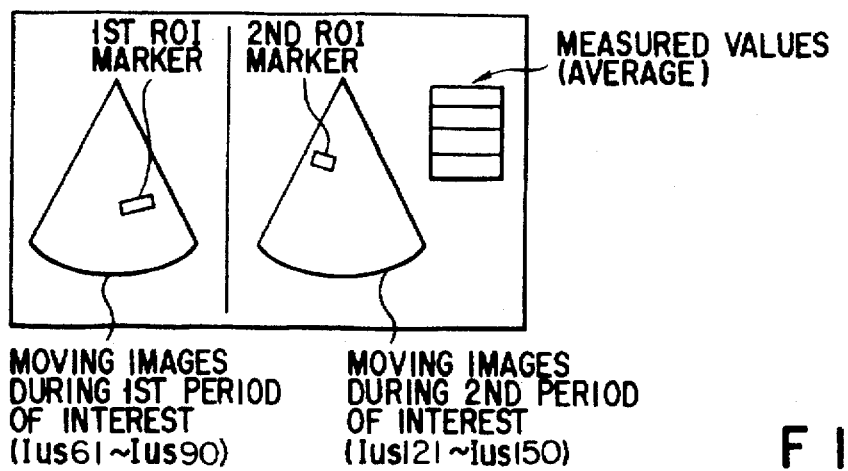

The following application of the present invention is possible. As shown in FIGS. 7A and 7B, it is possible to set up first and second periods of interest (two heart beat periods) and set up an ROI marker for each of the two periods of interest. In this case, as shown in FIG. 7C, ultrasonic image data during the first and second periods are combined into one frame in the DSC 13, moving images within each period are displayed separately, and measured values are obtained with each period. In addition, the average of measured values in the first and second periods may be calculated.

Although the preferred embodiment of the present invention has been disclosed and described, it is apparent that other embodiments and modifications are possible.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. An ultrasound diagnostic apparatus comprising:
   means for repeatedly scanning a plane section of a human body under examination by ultrasound waves with a given cycle to thereby obtain receiving signals;
   ultrasonic image producing means responsive to said receiving signals for successively producing ultrasonic images with said given cycle;
   storing means for storing ultrasonic images with time information;
   setting means for setting a period of interest;
   readout means connected to said setting means responsive to said set period of interest for sequentially and selectively reading ultrasonic images which are a part of said stored ultrasonic images corresponding to said period of interest from said storing means with said given cycle so that said read ultrasonic images are repeatedly displayed as moving images;
   overlaid image producing means for producing an overlaid image containing an ROI marker and repeatedly outputting said overlaid image with said given cycle;
   combining means connected to said storing means and said overlaid image producing means for combining each of said ultrasonic images corresponding to said period of interest and said overlaid image for said period of interest;
   displaying means for displaying said ultrasonic images combined with said overlaid image as moving images;
   position changing means for changing the position of said ROI marker in said overlaid image so that said ROI marker will shift on said moving images; and
   measuring means for obtaining measured values in the position of said ROI marker.

2. The apparatus according to claim 1, wherein said measuring means obtains measured values in the same position of said ROI marker for each of said ultrasonic images corresponding to said period of interest.

3. The apparatus according to claim 1, wherein said measuring means obtains measured values for each of said ultrasonic images corresponding to said period of interest, and said overlaid image producing means includes said measured values into said overlaid image so that said measured values are sequentially displayed with said moving images.

4. The apparatus according to claim 1, wherein said ultrasonic image producing means produces blood flow images as said ultrasonic images, and said measuring means obtains blood flow information as said measured values on the basis of pixel values of a pixel group in said blood flow images which corresponds in position to said ROI marker.

5. The apparatus according to claim 1, wherein said measuring means obtains said measured values on the basis of pixel values of a pixel group in said ultrasonic images which corresponds in position to said ROI marker.

6. The apparatus according to claim 1, wherein said measuring means measures at least one of distance, area, and capacity on the basis of the position of said ROI marker.

7. The apparatus according to claim 1, wherein said measuring means obtains said measured values for each of said ultrasonic images and produces a time curve representing changes of said measured values with respect to time.

8. The apparatus according to claim 1, wherein said overlaid image producing means produces an overlaid image containing a first ROI marker and a second ROI marker, said position changing means changes the position of said first ROI marker and the position of said second ROI marker individually, and said measuring means obtains said measured values in each of the positions of said first and second ROI markers.

9. The apparatus according to claim 1, wherein said setting means sets a first period of interest and a second period of interest, said readout means reads first ultrasonic images produced during said first period of interest and second ultrasonic images produced during said second period of interest, and said combining means combines said first ultrasonic images and said second ultrasonic images on a frame-by-frame basis so that said first and second ultrasonic images are simultaneously displayed as moving images on the same display screen.

* * * * *